(12) United States Patent
Fairley et al.

(10) Patent No.: US 6,816,249 B2
(45) Date of Patent: Nov. 9, 2004

(54) HIGH THROUGHPUT BRIGHTFIELD/ DARKFIELD WAFER INSPECTION SYSTEM USING ADVANCED OPTICAL TECHNIQUES

(75) Inventors: Christopher R Fairley, San Jose, CA (US); Tao-Yi Fu, Fremont, CA (US); Gershon Perelman, Cupertino, CA (US); Bin-Ming Benjamin Tsai, Saratoga, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 09/907,295

(22) Filed: Jul. 17, 2001

(65) Prior Publication Data

US 2002/0118359 A1 Aug. 29, 2002

Related U.S. Application Data

(63) Continuation of application No. 08/991,927, filed on Dec. 16, 1997, now Pat. No. 6,288,780, which is a continuation-in-part of application No. 08/884,467, filed on Jun. 27, 1997, now Pat. No. 5,822,055, which is a continuation of application No. 08/489,019, filed on Jun. 6, 1995, now abandoned.

(51) Int. Cl.[7] .............................................. G01N 21/00
(52) U.S. Cl. ................................ 356/237.1; 356/239.1; 356/394
(58) Field of Search ............................ 356/237.1–237.5, 356/239.1, 394; 348/125, 126; 250/559.46, 559.39, 559.41, 559.45; 382/149, 210, 143, 144, 145

(56) References Cited

U.S. PATENT DOCUMENTS

| | | | |
|---|---|---|---|
| 4,772,126 A | | 9/1988 | Allemand et al. |
| 4,877,326 A | | 10/1989 | Chadwick et al. |
| 5,038,048 A | * | 8/1991 | Maeda et al. .......... 250/559.41 |
| 5,177,559 A | * | 1/1993 | Batchelder et al. ....... 356/237.5 |
| 5,278,012 A | * | 1/1994 | Yamanaka et al. ............. 430/30 |
| 5,293,538 A | * | 3/1994 | Iwata et al. ............... 356/239.1 |
| 5,446,542 A | * | 8/1995 | Muraoka ...................... 356/400 |
| 5,455,870 A | * | 10/1995 | Sepai et al. .................. 382/147 |
| 5,469,294 A | * | 11/1995 | Wilt et al. ................... 359/436 |

(List continued on next page.)

FOREIGN PATENT DOCUMENTS

| | | |
|---|---|---|
| WO | WO 00/77500 | 12/2000 |
| WO | WO 01/13098 A1 | 2/2001 |

*Primary Examiner*—Hoa Q. Pham
(74) *Attorney, Agent, or Firm*—Smyrski & Livesay, LLP

(57) ABSTRACT

The broadband brightfield/darkfield wafer inspection system provided receives broadband brightfield illumination information via a defect detector, which signals for initiation of darkfield illumination. The defect detector forms a two dimensional histogram of the defect data and a dual mode defect decision algorithm and post processor assess defects. Darkfield radiation is provided by two adjustable height laser beams which illuminate the surface of the wafer from approximately 6 to 39 degrees. Each laser is oriented at an azimuth angle 45 degrees from the orientation of the manhattan geometry on the wafer, and 90 degrees in azimuth from one another. Vertical angular adjustability is provided by modifying cylindrical lens position to compensate for angular mirror change by translating an adjustable mirror, positioning the illumination spot into the sensor field of view, rotating and subsequently moving the cylindrical lens. A brightfield beamsplitter in the system is removable, and preferably replaced with a blank when performing darkfield illumination. Light level control for the system is provided by a dual polarizer first stage. Light exiting from the second polarizer passes through a filter which absorbs a portion of the light and comprises the second stage of light control. The beam then passes through a polarizing beamsplitter. The second channel is further reflected and polarized and both beams thereafter illuminate the substrate.

35 Claims, 9 Drawing Sheets

U.S. PATENT DOCUMENTS

| | | |
|---|---|---|
| 5,822,055 A | 10/1998 | Tsai et al. |
| 5,970,168 A | 10/1999 | Montesanto et al. |
| 6,078,386 A | 6/2000 | Tsai et al. |
| 6,091,492 A * | 7/2000 | Strickland et al. .......... 356/336 |
| 6,288,780 B1 | 9/2001 | Fairley et al. |

* cited by examiner

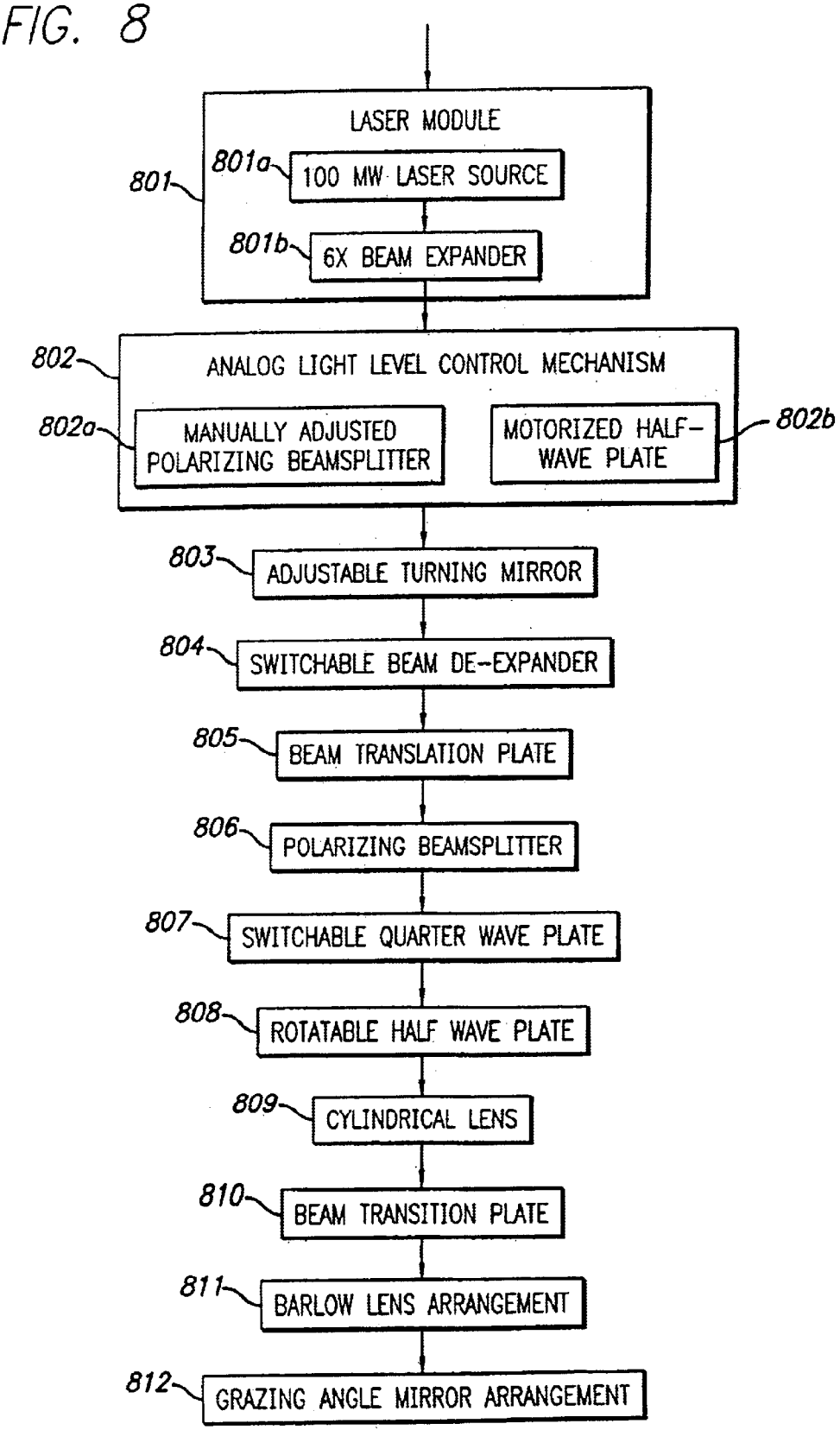

HIGH THROUGHPUT BRIGHTFIELD/ DARKFIELD WAFER INSPECTION SYSTEM USING ADVANCED OPTICAL TECHNIQUES

This is a continuation of application Ser. No. 08/991,927 filed Dec. 16, 1997, now U.S Pat. No. 6,288,780 which is a continuation-in-part of application Ser. No. 08/884,467, filed Jun. 27, 1997, now U.S. Pat. No. 5,822,055, issued Oct. 3, 1998, entitled "Optical Inspection of a Specimen Using Multi-Channel Responses from the Specimen," which is a continuation of U.S. patent application Ser. No. 08/489,019, filed on Jun. 6, 1995, now abandoned.

BACKGROUND OF THE INVENTION

1. Field of the Invention

The present invention relates generally to the art of optical inspection of semiconductor wafers, and more specifically to a high throughput brightfield and darkfield wafer inspection system having image processing redirected from the mechanical and electronics segments of the inspection system to the optical domain.

2. Description of the Related Art

Semiconductor wafer inspection techniques have historically utilized brightfield illumination, darkfield illumination, or spatial filtering. Brightfield imaging is not generally sensitive to small particles. Brightfield imaging tends to scatter small particles away from the collecting aperture, thereby resulting in reduced returned energy. When a particle is small compared to the optical point spread function of the lens and small compared to the digitizing pixel, the brightfield energy from the immediate areas surrounding the particle typically contribute a large amount of energy. The small reduction in returned energy resulting from the small particle makes the particle difficult to detect. Further, the small reduction in energy from a small particles often masked out by reflectivity variations from the bright surrounding background such that small particles cannot be detected without numerous false detections. Additionally, if the small particle is on an area of low reflectivity, which may occur for some process layers on wafers and always for reticles, photomasks, and flat panel displays, the resultant background return is low and any further reduction due to the presence of a particle becomes very difficult to detect.

Newer systems utilize broadband brightfield imaging as opposed to traditional monochromatic or narrow band brightfield imaging. Broadband brightfield imaging minimizes contrast variations and coherent noise present in narrow band brightfield systems, but are not sensitive to small particles.

Darkfield imaging is employed to detect small particles on wafers, reticles, photomasks, flat panels, and other specimens. The advantage of darkfield imaging is that flat specular areas scatter very little light back toward the detector, resulting in a dark image. Darkfield illumination provides a larger pixel-to-defect ratio, permitting faster inspections for a given defect size and pixel rate. Darkfield imaging also permits fourier filtering to enhance signal to noise ratios.

Any surface features or objects protruding above the surface of the object scatter more light toward the detector in darkfield imaging. Darkfield imaging thus produces a dark image except where circuit features, particles, or other irregularities exist. Particles or irregularities are generally assumed to scatter more light than circuit features. However, while this assumption permits a thorough inspection for particles on blank and unpatterned specimens, in the presence of circuit features a darkfield particle inspection system can only detect large particles which protrude above the circuit features. The resulting detection sensitivity is not satisfactory for advanced VLSI circuit production.

While some attempts to improve darkfield performance have been attempted, such systems tend to have drawbacks, including drawbacks resulting from the very nature of darkfield illumination. For example, while brightfield illumination floods the entire field of view with light, darkfield illumination is confined to a narrow strip of light. Due to the nature of lasers, the application of light in darkfield illumination tends to be non-uniform and limits the amount of data which can be collected in a particular time period.

Some imaging systems currently available attempt to address problems associated with darkfield imaging. One instrument, manufactured by Hitachi, uses the polarization characteristics of the scattered light to distinguish between particles and normal circuit features, based on the assumption that particles depolarize light more than circuit features during the scattering process. When circuit features become relatively small (less than or on the order of the wavelength of light), the circuit can depolarize the scattered light as much as the particles. As a result, only larger particles can be detected without false detection of small circuit features.

Further, a system employing a combination of a monochromatic darkfield and a monochromatic brightfield imaging for wafer inspection is poorly adapted for inspecting Chemical Mechanaical Planarized (CMP) wafers, which often have film thickness variations and a grainy texture. Grainy texture, it should be noted, may also be a result of the metal grain structure of the wafer.

Another attempt to resolve problems associated with darkfield imaging positions the incoming darkfield illuminators such that the scattered light from circuit lines oriented at 0°, 45°, or 90° are minimized. This method is generally effective on circuit lines, but light scattering from corners is still relatively strong. Further, detection sensitivity for areas having dense circuit patterns must be reduced to avoid the false detection of corners.

Prior systems for processing brightfield and darkfield data have relied on different processing techniques. The system of FIG. 1 illustrates a prior system which performed a full processing of a wafer using brightfield imaging followed by darkfield imaging and subsequent processing of the wafer. The problem with this mechanization is that throughput, or the time to process a single wafer, is generally poor, and it does not have the capability to use the combined results from both brightfield and darkfield imaging. As shown in FIG. 1, brightfield imaging 101 is performed on wafer 103, wherein the brightfield imaging has tended to be either monochromatic or narrow band imaging. The wafer image is received via sensor 104, which performs TDI, or Time Delay Integration, and a phase lock loop analog to digital conversion (PLLAD). Data is then directed to input buffer 105, which passes data to defect detector 107. Defect detector 107 uses delay 106 to perform a die-to-die or cell-to-cell comparison of the brightfield image processed wafer 103. The results are then passed to post processor 108 where brightfield defects are determined and passed. The wafer 103 is then illuminated using darkfield illumination 102 in the second run, and all subsequent processes are performed on the darkfield image. The result of this second run is a list of darkfield defects. The typical defect assessment performed by the defect detector and the post processor 108 is to set a threshold above which a feature is considered a defect, and only passing brightfield or darkfield results exceeding such thresholds. This does not completely account for the benefits associated with the combined effects of using brightfield and darkfield, and the amount of time necessary to perform all processing for a single wafer can be significant.

An alternative to the mechanization of FIG. 1 is presented in FIG. 2. The system of FIG. 2 illustrates simultaneous brightfield illumination 201 and darkfield illumination 202 of wafer 203. The simultaneous illumination is typically from a single illumination source, and the system receives the wafer images using dual TDI and PLLAD sensors 204 and 204'. Each sensor 204 and 204' receives an image of wafer 203 and loads a signal representing that image into input buffer 205 or 205', such as RAM. From buffer 205 or 205' the system feeds data to defect detector 207 where data representing the wafer 203 is compared to similar or reference wafer characteristics under the control of delays 206 and 206'. Delays 206 and 206' each provide timing for a die-to-die or cell-to-cell comparison by defect detector 207. Defect detector 207 uses information from both brightfield and darkfield illumination steps to determine the location of defects on wafer 203. The combined defect list from defect detector 207 is then evaluated using post processor 208 to identify pattern defects and particles.

The drawback in implementing the system illustrated in FIG. 2 is that individual TDI and PLLAD sensors 204 and 204', input buffers 205 and 205', and delays 206 and 206' are highly sophisticated and expensive components, and the use of two of each such components significantly increases the cost of the entire machine. Further, performance of defect detector 207 and post processor 208 requires that all data be available and be evaluated at one time, which can cause significant delays and high processing costs. For example, it is not unusual to see brightfield imaging requiring a very short amount of time while darkfield imaging takes significantly longer. This system also uses monochromatic or narrowband brightfield imaging, which has a tendency to exhibit undesirable contrast variations and coherent noise problems as discussed above.

Spatial filtering is another technique used to enhance the detection of particles. With plane wave illumination, the intensity distribution at the back focal plane of a lens is proportional to the Fourier transform of the object. Further, for a repeating pattern, the Fourier transform consists of an array of light dots. Placement of a filter in the back focal plane of the lens to block out the repeating light dots permits filtering of the repeating circuit pattern and leaves only non-repeating signals, such as particles or other defects. The major limitation of spatial filtering is that only areas having repeating areas or blank areas may be inspected.

There has been little interest in combining brightfield and darkfield techniques due to a lack of understanding of the advantages presented by such a technique. All of the machines currently available employing monochromatic brightfield/darkfield imaging use a single light source for both brightfield and darkfield illumination and do not use a combination of brightfield and darkfield images to determine defects.

Microscopes exist on the market today which combine both monochromatic brightfield and darkfield illumination, and such microscopes have a single light source and provide both illuminations simultaneously, thus making it impossible to separate the brightfield and darkfield results. Such mechanizations simply result in a combined full-sky illumination.

A further limitation of prior systems is that the illumination sources tend to be fixed in place, which also fixes the ability of the system to pick up defects in surfaces or specimens having different physical properties. Typically, a video camera is positioned above the specimen and light is applied to the specimen at a predetermined angle. The application of light to a particle tends to scatter the light, which is then detected by the video camera. If the specimen contains an irregular surface configuration, such as excess material or a semiconductor pattern, the fixed angle of the light source may not optimally scatter the applied light, inhibiting the ability to detect defects. Even for a wafer having a regular semiconductor pattern, orientation of the illumination source provides a different return when a pattern feature is oriented at 0°, 45°, or 90°. Also, the support mechanisms and circuitry associated with the light source tend to be large and bulky, thereby impeding the repositioning capability of the light source.

Another problem with brightfield/darkfield imaging is the use of imaging devices within the same physical space. Components associated with brightfield imaging are generally used for darkfield imaging as well, and several overlapping components exist when using both forms of illumination and detection. However, due to the optical, physical, and other characteristics of components used in brightfield/darkfield imaging, some components tend to provide advantages with one form of illumination and disadvantages for the other illumination scheme. The minimization of the disadvantages associated with a form of imaging improves the ability to detect problems associated with individual specimens.

Another problem associated with wafer inspection systems is the control of light level. Control of light level is particularly complex and critical where a high level of light collection efficiency is desired, and where the gain of the detector is not readily controlled. Prior systems for providing light level control for wafer inspection include providing absorbing glass in the illumination path, and control over the output energy of the laser. These systems either do not perform sufficiently and/or are too costly or complex to use efficiently.

It is therefore an object of the current invention to provide a system for detecting defects on a wafer, the system having the ability to detect defects beyond those detectable using monochromatic or narrowband brightfield imaging alone. Inherent in such a system would be the ability to minimize contrast variations and coherent noise problems.

It is another object of the current invention to provide a system for detecting defects which has the ability to detect small particles, including particles having a size smaller than the wavelength of light, with a minimum number of false detections. The system should provide for a minimum number of components to decrease overall cost and provide for maximum throughput of specimens.

It is yet another object of the current invention to provide a system which provides the ability to perform an accurate inspection of Chemical Mechanaical Planarized (CMP) wafers, or other specimens having film thickness variations or grainy textures.

It is still another object of the current invention to provide a system for detecting defects on a wafer wherein the system has the ability to optimize the incidence of light reflected from specimens having various surface characteristics.

It is still another object of the current system to provide both brightfield and darkfield illumination using a minimum number of components in a minimum amount of physical space while simultaneously minimizing adverse effects associated with brightfield and darkfield illumination.

It is still another object of the current invention to provide an efficient method or apparatus for light level control in the wafer inspection system.

SUMMARY OF THE INVENTION

According to the present invention, there is provided a broadband brightfield/darkfield wafer inspection system. Broadband brightfield illumination illuminates a wafer, and data from this illumination is captured by a sensor. The sensor is preferably a TDI sensor having PLLAD capability, but other sensors, such as a non-integrating CCD or linear sensor may be employed. The sensor thereupon loads a signal representative of the image into an input buffer, which feeds data to a defect detector, where the broadband brightfield data from the sample being inspected is compared to a similar sample or reference wafer using timing control from a delay. The defect detector signals initiation of darkfield illumination of the wafer.

The sensor captures illumination resulting from darkfield illumination and loads a signal representative of the image into the input buffer, which feeds data to the defect detector. Darkfield data in a similar manner to broadband brightfield data using the delay. Darkfield illumination data from the defect detector is then passed to post processor.

The defect detector signals commencement of the darkfield imaging based on the type of wafers presented and the expected timing associated with the wafers. Broadband brightfield and darkfield data does not overlap along the system path, and the time associated with processing the combined broadband brightfield and darkfield data is minimized.

The defect detector includes a 2D histogram circuit which forms a two dimensional histogram of the defect data with brightfield differences plotted on one axis and darkfield differences plotted on the orthogonal axis. The histogram information is then applied to a dual mode defect decision algorithm, which sizes and locates defects resulting from the brightfield and darkfield inspections. The post processor evaluates the quality and importance of the detected defects. Ideally, the dual mode defect decision algorithm and post processor exclude predictable variations without identifying them as defects, and identifies other responses outside an expected range to be defects, and broadband brightfield and darkfield data may be combined and used to accomplish this intent.

Darkfield radiation is provided by two adjustable height laser beams. The laser beams illuminate the surface of the wafer at an angle of approximately 6 to approximately 39 degrees. The first laser is oriented at an azimuth angle 45 degrees greater than the orientation of the manhattan geometry on the wafer, and the second laser is oriented at an azimuth angle 45 degrees less than the manhattan geometry on the wafer, or 90 degrees offset from the first laser.

Darkfield illumination within the system accommodates three elevation angles to provide varying ability to illuminate the wafer. At the high grazing angle setting, 39 degrees, the best sensitivity for low noise wafers such as smooth film and early etch specimens is available. The low grazing angle setting, 6 degrees, provides some attenuation of noise from the wafer pattern or from wafer roughness. The 20 degree grazing angle illumination is a compromise setting which offers a tradeoff between the sensitivity benefit of the 39 degree angle and the noise reduction of the 6 degree angle.

While the elevation grazing angle settings include 6, 20, and 39 degree settings, the mechanization of the current invention provides for a continuously variable angular offset, and thus the elevation grazing angle may vary anywhere from approximately five to approximately 45 degrees.

The apparatus providing the adjustable angle uses a rotating cylindrical lens to control the angular orientation of the laser spot, a pixel size changer, and an adjustable mirror. The angle of the adjustable mirror is altered to change the angle of incidence of each of the lasers on the wafer. The position of the cylindrical lens is modified to compensate for that change and maintain the elliptical spot in the correct position relative to the surface of the wafer and sensor.

The system can compensate for mirror rotation by moving, rotating, or moving and rotating the cylindrical lens. The preferred method is to translate the adjustable mirror in the vertical direction, normal to the wafer, to position the illumination spot into the sensor field of view, to rotate the cylindrical lens to properly orient the ellipse, and finally to move the cylindrical lens to obtain desired ellipticity.

The brightfield beamsplitter provided is removable, and preferably replaced with a blank, or glass, when performing darkfield illumination. This allows more light to pass to sensor and permits greater levels of detection in darkfield imaging. An alternative method for producing the same result is to perform brightfield imaging in a selected color light spectrum and performing darkfield in a different frequency light spectrum, such as red being selected for brightfield illumination and green for darkfield illumination.

Light level control for the system is provided by a dual polarizer first stage, wherein the polarizers are rotated relative to one another to control the intensity of the beam passing through them. The relative rotation of the polarizers provides variation of the beam intensity in a continuous manner, preferably without varying the polarization of the beam. Rotation of the second polarizer controls the balance between the two output channels. Light exiting from the second polarizer passes through a filter, which is preferably a discrete glass filter, and which absorbs a portion of the light and comprises the second stage of light control.

The beam then passes through a polarizing beamsplitter, which divides the light into first and second channels. The second channel is further reflected and polarized, as needed, and both beams thereafter illuminate the substrate. Both beams preferably have equal intensity as they impinge on the substrate surface.

Other objects, features, and advantages of the present invention will become more apparent from a consideration of the following detailed description and from the accompanying drawings.

DESCRIPTION OF THE DRAWINGS

FIG. 8 presents a functional depiction of the components used in darkfield imaging;

DETAILED DESCRIPTION OF THE INVENTION

Figure 1:
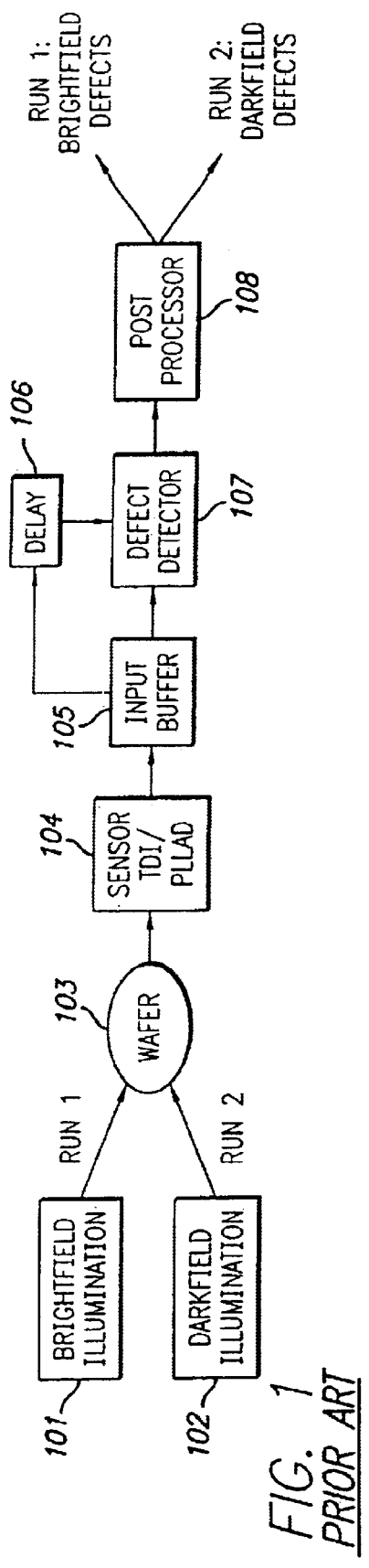
FIG. 1 illustrates a prior system which performed a full processing of a wafer using brightfield imaging followed by darkfield imaging.
Figure 2:
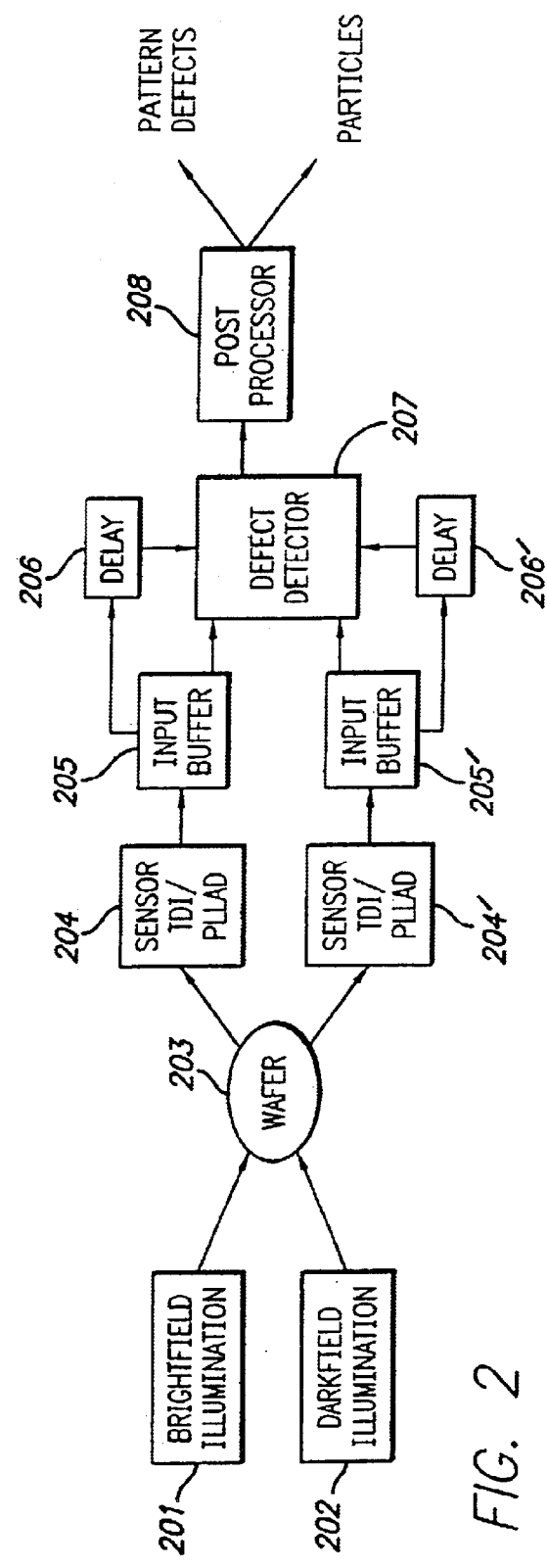
FIG. 2 is a system using parallel processing of brightfield and darkfield data.

The inventive system herein combines large pixel DDF (Directional Dark Field) illumination with broadband brightfield illumination to enable increased sensitivity to previous brightfield systems at higher throughput with reduced image computing power. The system includes a dual darkfield illumination module, providing two laser illumination beams having adjustable grazing angle, light level, and polarization.

Darkfield imaging collects scattered light from a defect, while brightfield imaging collects reflected light. At a given pixel size, a very small (sub-pixel) imaging system averages everything seen in the pixel, including defect plus background. Brightfield imaging uses a small enough pixel to resolve the edges of the defect and thereby detect a contrast. Darkfield imaging averages everything contained in a pixel, but the background is always black, and even small defects have a tendency to scatter large amounts of light. A flat, opaque defect may scatter very little light in darkfield, but may provide obvious contrast in brightfield. Small, transparent defects may scatter efficiently in darkfield illumination, but may be very difficult, if not impossible, to detect in brightfield. Darkfield imaging is generally useful in detecting defects having specific height, depending upon interaction between illumination with the geometry and effects due to transparent layers on the specimen.

Because darkfield illumination impinges on the wafer at a grazing angle, the darkfield illumination system better discriminates against previous layer defects. An adjustable grazing angle permits a tradeoff absolute sensitivity for background noise rejection. At generally low grazing angles, the scatter from surface roughness and from the wafer geometry is reduced, permitting a higher signal-to-noise ratio in the presence of roughness or pattern noise.

Directional darkfield technology provides two distinct advantages: a larger pixel/defect ratio and fourier filtering.

A higher pixel/defect ratio permits inspection of more wafers and the detection of smaller defects. Image computer cost is proportional to pixel rate, and larger pixels permits the inspection of more wafers inspected per unit time. Required pixel rate increases inversely with the square of pixel size, thereby translating into less expensive inspection systems, or more wafers inspected. A higher pixel/defect ratio provides the ability to detect smaller defects.

The system disclosed herein uses coherent, directional illumination, or a laser with discrete illumination directions. This optical technique enables two optical filtering techniques, namely azimuth filtering and fourier filtering. Fourier filtering is discussed and used herein in accordance with currently pending U.S. patent application Ser. No. 08/906,621, to Steve Montesanto, Gershon Perelman, and Rudolf Brunner, entitled "Fourier Filtering Mechanism for Inspecting Wafers", filed Aug. 5, 1997, the entirety of which is incorporated herein by reference.

Azimuth filtering refers to the ability to reject the scatter from Manhattan geometry (straight line geometry parallel to the rectangular die edges) by bringing the laser illumination 45 degrees in azimuth to the die edges. The scatter from the Manhattan geometry is not collected in the imaging system; the straight line Manhattan routes disappear under the darkfield illumination of the present system. Scatter from the approximately 45 degree routes are not filtered by the optics of the current invention, and azimuth filtering ceases to operate effectively once the numerical aperture (NA) of the objective exceeds approximately 0.707. When the NA of the objective exceeds approximately 0.707, the scatter from the Manhattan geometry falls within the collection cone of the imaging system. Wafer layers having considerable roughness on the edges of the geometry will mitigate the effect of azimuth filtering.

The coherent nature of the inventive system described herein provides for improved optical filtering on the array portion of wafer geometries. Illuminating a coherent array with coherent light results in a coherent diffraction pattern, some of which is collected by the imaging optics. The diffraction pattern from an array at the wafer appears as an array of spots at the fourier plane of the imaging path. By putting adjustable mechanical blockages in the fourier plane, these spots are filtered out, effectively removing the repeating array content from the image. A fourier filtered array image appears devoid of all repeating content, Manhattan or otherwise. The signal to noise ratio in such an array can be dramatically increased compared to the SNR without the filter. Without the filter, the array may have efficient scattering properties, permitting only relatively low light levels before the TDI sensor, described below, is taken to saturation. With the filter in place, the system can completely eradicate the scatter from the array, thereby providing a large increase in light level, and a resultant improvement in the sensitivity in the array area. This is impossible to attain in non-laser brightfield systems, since such systems have incoherent illumination. The improved sensitivity resulting from filter placement is difficult to duplicate for scanning laser systems, either brightfield or darkfield, since it requires that the illumination spot be large enough to illuminate several cells of the repeating geometry.

Figure 3:
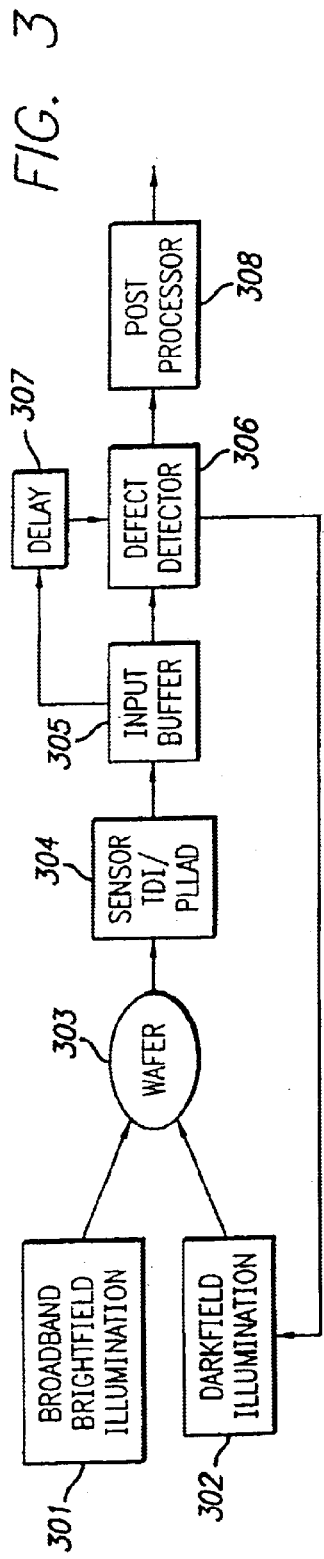
FIG. 3 presents an overall block diagram of the wafer inspection system disclosed herein.

FIG. 3 illustrates an overall block diagram of the inventive inspection system disclosed herein. Broadband brightfield illumination 301 illuminates the wafer 303, and data from this illumination is captured by sensor 304. Sensor 304 is preferably a TDI sensor having PLLAD capability, but other sensors, such as a non-integrating CCD or linear laser could be used. The sensor 304 thereupon loads a signal representative of the image into input buffer 305, which may be RAM. Input buffer 305 feeds data to defect detector 306, where the broadband brightfield data from the sample being inspected is compared to a similar sample or reference wafer using control of delay 307. Delay 307 provides the timing to allow for a die-to-die or cell-to-cell comparison by defect detector 306. Defect detector 306 then signals initiation of darkfield illumination 302 of wafer 303.

Sensor 304 captures illumination resulting from darkfield illumination 302. The sensor 304 loads a signal representative of the image into input buffer 305. Input buffer 305 feeds data to defect detector 306, where the darkfield data from the sample being inspected is compared to a similar sample or reference wafer using control of delay 307. Delay 307 provides the timing to allow for a die-to-die or cell-to-cell comparison by defect detector 306. Darkfield illumination data from defect detector 306 is then operated upon with the broadband brightfield data and the results are passed to post processor 308.

Figure 4:
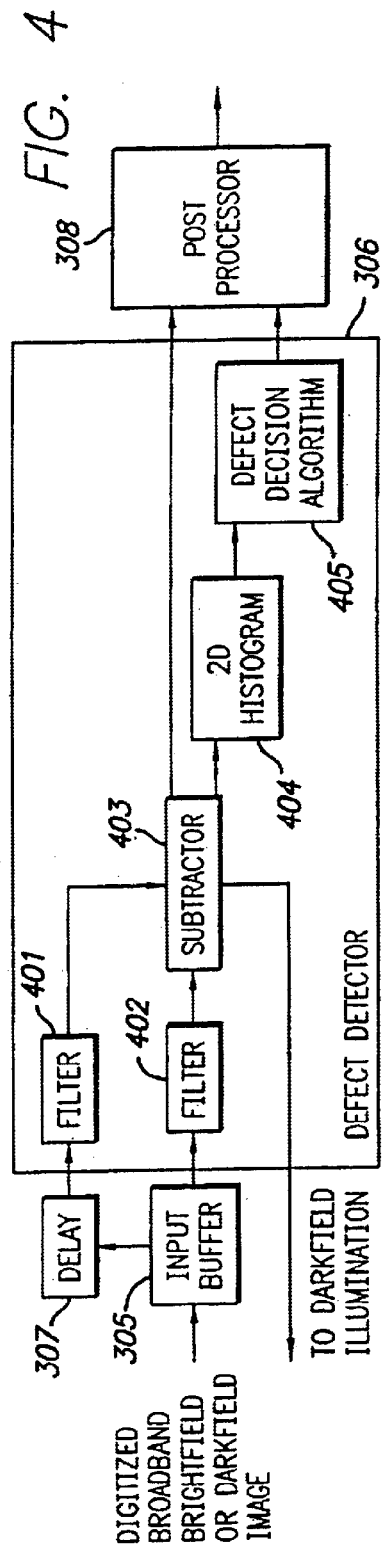
FIG. 4 illustrates the components of the defect detector.

The components of defect detector 306 are illustrated in FIG. 4. The digitized image, either brightfield or darkfield, passes to input buffer 305, which passes data to delay 307 and also to input buffer 402. Delay 307 passes timing information to delay filter 401. Each of the filters 401 and 402 are used to preprocess the image data and can be implemented as a 3 by 3 or 5 by 5 pixel digital filter. While the filters could be implemented as any digital filter having square or rectangular dimensions, including a 4 by 4, 6 by 6, or 7 by 7 pixel filter, the 3 by 3 or 5 by 5 pixel digital filter is preferred. The system applies preprocessed images from filters 401 and 402 to subtractor 403, where ideal brightfield images are compared with the delayed version of the current specimen. The subtractor 403 then may signal to the system that darkfield imaging may proceed. Depending on the time required for brightfield imaging and loading into 2D histogram circuit 404, darkfield imaging may alternately be initiated at a prior point in the procedure, such as once data is loaded into input buffer 305, or under other advantageous timing conditions which would promote overall efficiency.

Based on the type of wafers presented and the expected timing associated with the wafers, an indication to commence darkfield processing should occur such that brightfield and darkfield data does not overlap along the system path and the time associated with 2D histogram 404 awaiting darkfield data is minimized. An alternative method for accomplishing this goal would be to commence darkfield imaging at a predetermined time after brightfield imaging is completed.

Darkfield illumination 302 is performed on the wafer 303, which is received by sensor 304 and passed to input buffer 305 and delay 307. Darkfield imaging data passes to defect detector 306 from input buffer 305 and delay 307 via filter 401 and filter 402, and thereafter passes to subtractor 403 which compares ideal darkfield images to the delayed version of the subject wafer. The subtractor 403 passes the darkfield data to 2D histogram circuit 404. 2D histogram circuit 404 forms a two dimensional histogram of the defect data with brightfield differences plotted on one axis and darkfield differences plotted on the orthogonal axis. The histogram information is then applied to a dual mode defect decision algorithm 405.

Dual mode defect decision algorithm 405 sizes and locates defects resulting from the brightfield and darkfield inspections, while post processor 308 evaluates the quality and importance of the detected defects. Different methods may be employed by the dual mode defect decision algorithm 405 and post processor 308 to detect significant defects. Semiconductor wafers often exhibit surface features such as contrast variations, grain and grain clusters, or process variations such as chemical smear. Each of these anomalies do not generally impact the performance of a die produced on such a wafer, but can be a concern under some circumstances. Each of these surface features also has a typical range of brightfield and darkfield readings associated therewith. Additionally, noise is associated with system operation, and this noise can cause variations in brightfield and darkfield difference signals.

Ideally, the dual mode defect decision algorithm 405 and post processor 308 exclude predictable variations without identifying them as defects, and identifies other responses outside an expected range to be defects. In the current system, this may be accomplished in a number of ways. The preferred implementation is that for a defect having a magnitude exceeding a threshold value for either brightfield or darkfield illumination, the defect is considered of concern and passed from the dual mode defect decision algorithm 405 and post processor 308. The system may evaluate particular characteristics detectable by brightfield illumination, such as those defects scattering little light, and other characteristics detectable by darkfield illumination, such as a heightened irregularity, and base results only on a combination of both effects. False readings could be reduced by requiring both brightfield and darkfield readings exceeding particular thresholds Other mechanizations, depending on the types of defects generally found in the specimens, may be utilized while still within the course and scope of this invention.

Defect detector 306 and, in particular, defect decision algorithm 405, therefore determine whether a defect exists, based on known defect characteristics and machine limitations, irrespective of the size or quality of such defect, while post processor 308 determines whether the defect is relatively significant. The post processor 308 also receives data from subtractor 403.

Dual mode post processor 308 can be based on any high performance post processor board, such as a Motorola 68040 CPU based VME (Virtual Machine Environment) board.

Figure 5:
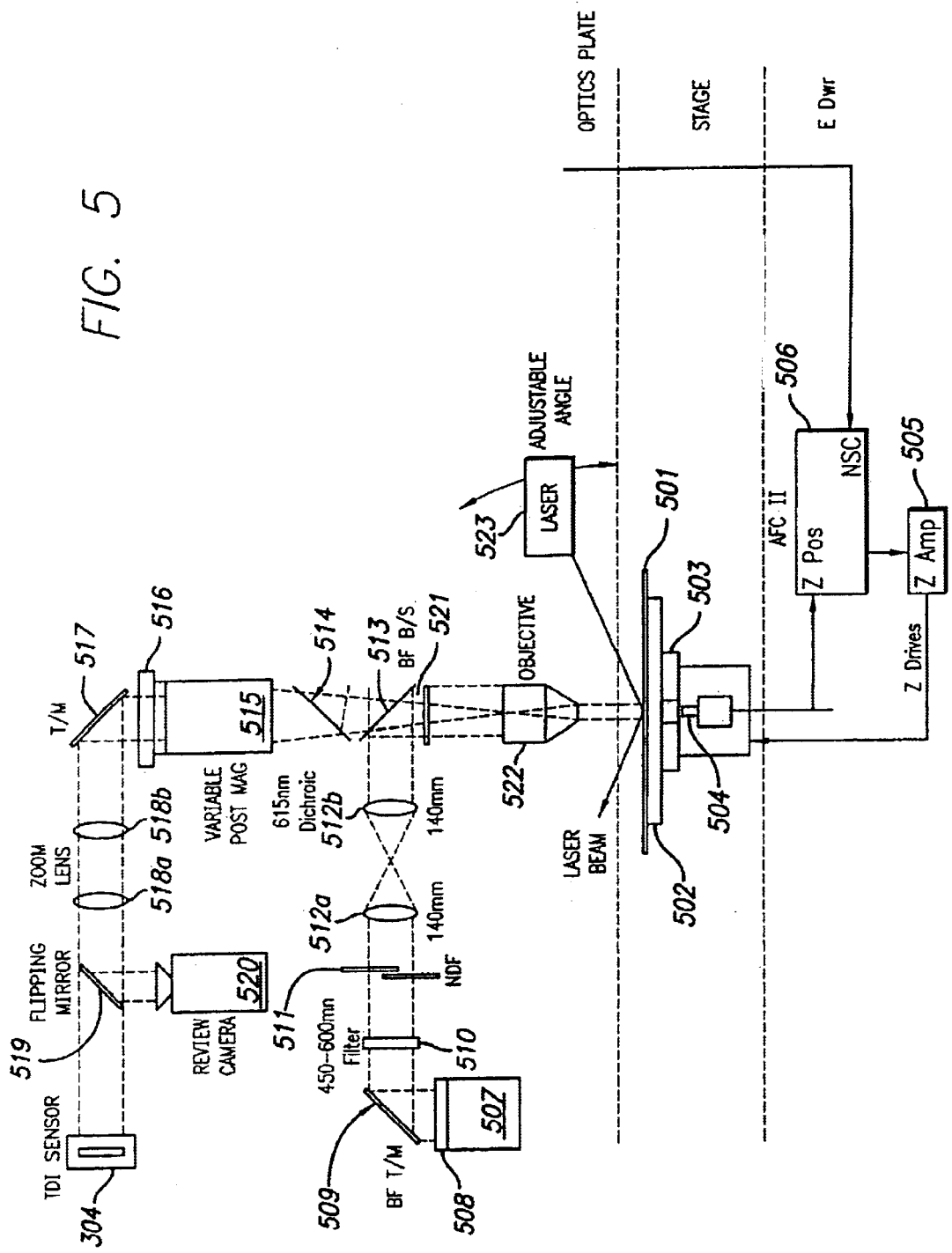
FIG. 5 is a side view schematic of the broadband brightfield/darkfield wafer inspection system.

Another view of the system is presented in the simplified schematic diagram of FIG. 5. Wafer 501 lies on chuck 502 which interacts with theta brake 503 and ECS head 504. A feedback loop between the drive unit 506, drive amplifier 505, and the ECS head 504 provides a uniform movement of the components and wafer 501 based on a control signal received from the optics plate. The wafer is illuminated in brightfield using brightfield illuminator 507 having illuminator lens arrangement 508, brightfield turning mirror 509, first filter 510, ND (neutral density) filter 511, and dual lens arrangement 512a and 512b. Broadband brightfield light passes from dual 140 mm lens arrangement 512a and 512b to brightfield beamsplitter 513, which passes some light and reflects other light through turret turning mirror 521. Light thereupon passes through objective 522, which contains a condensing lens to focus the light, and thereupon onto wafer 501. Light is reflected from wafer 501 back through objective 522, turret turning mirror 521, brightfield/darkfield beamsplitter arrangement 513, and through 615 nm dichroic mirror 514, variable post mag 515, fourier filter 516, upper turning mirror 517, zoom lens arrangement 518a and 518b, and flipping mirror 519 to review camera 520 and sensor 304. Brightfield/darkfield beamsplitter arrangement 513 is discussed below.

First filter 510 is preferably an approximately 450–600 nm filter, while dual lens arrangement 512a and 512b is preferably a 140 mm lens, but similar components having features outside these ranges may be employed if they produce similar filtering and optical effects.

Under darkfield illumination, adjustable angle laser arrangement 523 directs at least one laser beam, and preferably two laser beams over the wafer 501 at a variable angle, where refraction from the wafer passes through objective 522, turret turning mirror 521, brightfield/darkfield beamsplitter arrangement 513, 615 nm dichroic mirror 514, variable post mag 515, fourier filter 516, upper turning mirror 517, zoom lens arrangement 518a and 518b, and flipping mirror 519 to review camera 520 and sensor 304.

Figure 6:
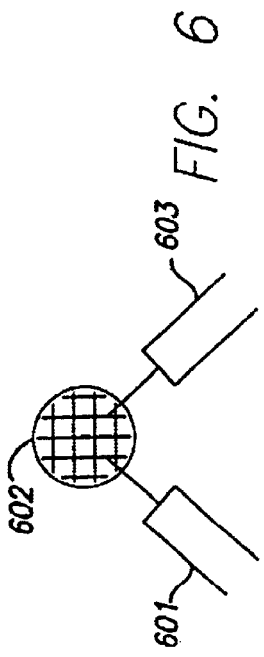
FIG. 6 is a vertical view of the orientation of the dual lasers relative to the wafer as used in darkfield illumination in the current system.

The system thereby includes both broadband brightfield and darkfield illumination. Monochromatic darkfield radiation is provided by two adjustable height laser beams. The laser beams illuminate the surface of the wafer at an angle of approximately 5 to approximately 45 degrees. As shown in FIG. 6, first laser 601 is oriented at an azimuth angle approximately degrees greater than the orientation of the manhattan geometry on the wafer 602, and the second laser 603 is oriented at an azimuth angle approximately 45 degrees less than the manhattan geometry on the wafer 602, or approximately 90 degrees offset from the first laser 601. These ranges could conceivably vary while still within the scope of the current invention. For example, slight offsets in the manhattan geometry or placement of lasers 601 and 603 significantly closer or further apart may produce beneficial effects depending on various factors.

The darkfield illumination system depicted in FIG. 5 serves several purposes. The system allows control of the elevation angle of the laser beams incident on the wafer, control over the polarization of the laser, control over the amount of laser power present in the field of view, and control over the shape of the beam within the field of view as a function of angle and pixel size. Darkfield illumination within the system of FIG. 5 accommodates elevation angles between 5 and 45 degrees, with settings for three elevation angles (6, 20, and 39 degrees) available. Darkfield illumination supports various pixel sizes, but preferably two pixel sizes (2.5 micrometers and 1.25 micrometers), and also preferably supports three polarization settings (S, P, and circular).

The laser is preferably a 100 mW frequency double diode-pumped YAG (DPY) operating at a wavelength of 532 nm, but other lasers having similar capabilities could be used while still within the scope of the present invention.

The system of FIG. 5 has continuously variable elevation angles to provide adjustable illumination of the wafer. At the a high grazing angle, such as an approximately 39 degree setting, the best sensitivity for low noise wafers such as smooth film and early etch specimens is available. In such situations the pattern scatter is low and little noise from surface roughness exists. The scattering efficiency of a given small defect increases as the illumination angle approaches normal incidence. At a low grazing angle, such as the approximately 6 degree setting, provides some attenuation of noise from the wafer pattern or from wafer roughness. This noise attenuation is not necessarily at comparable expense to the signal from defects on the wafer, so the signal to noise may be increased on some wafers where pattern and surface roughness dominate. The elevation effects are due to coherent illumination creating standing waves at the wafer surface, with a node (no field) at the wafer surface at equally spaced heights above it. As the illumination angle becomes more grazing, the spacing between nodes increases, such that surface roughness and patterns close to the wafer surface have low field strengths, and defects higher above the surface of the wafer have higher field strengths. The approximately 20 degree grazing angle setting offers a compromise setting which offers a tradeoff between the sensitivity benefit of the approximately 39 degree setting and the noise reduction of the approximately 6 degree setting. Again, within the scope of the current invention, as described herein, this angle may be altered continuously within the range of approximately 5 to approximately 45 degrees.

Figure 7:
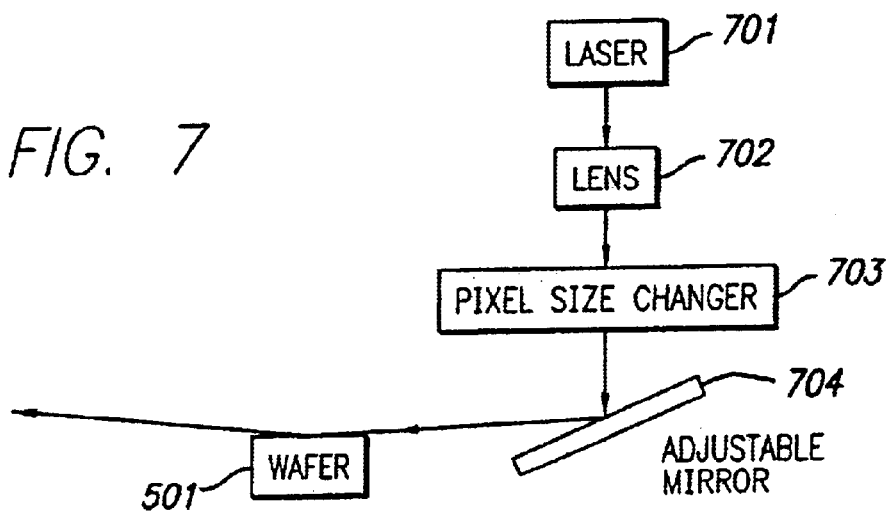
FIG. 7 illustrates the mechanization of the adjustable angle incidence of the dual laser beam arrangement used for darkfield illumination.

In order to provide the adjustable angle for the dual lasers 601 and 603, the apparatus presented in FIG. 7 is employed. The apparatus includes a laser 701 to produce laser beam 601 or 603, a rotating cylindrical lens 702 to control the angular orientation of the laser spot, a pixel size changer 703, and an adjustable mirror 704.

Light from laser 701 is shaped as an elliptical spot by rotating cylindrical lens 702. Pixel size is controlled by pixel size changer 703, while adjustable mirror 704 reflects the laser onto the surface of the semiconductor wafer 501. The angle of adjustable mirror 704 is altered to change the angle of incidence of the beam from each laser 601 or 603 on wafer 501. A simple mirror adjustment, without more, changes the position of the laser spot on the wafer 501, and also changes the shape and orientation of the elliptical spot on the wafer 501. This adjustment would cause the sensor 304 to image a portion of the wafer with poor illumination uniformity, or with very little illumination. Thus, the position of the cylindrical lens 702 is modified to compensate for that change and maintain the elliptical spot in the correct position relative to the surface of the wafer 501 and sensor 304.

The system can compensate for mirror rotation by moving cylindrical lens 702, rotating cylindrical lens 702, or both moving and rotating cylindrical lens 702. The preferred method is to translate mirror 704 in the vertical direction, normal to the wafer 501, to position the illumination spot into the sensor field of view, and to rotate cylindrical lens 702 to properly orient the ellipse, and finally to move the cylindrical lens 702 to obtain desired ellipticity.

The sensor 304 is preferably a TDI sensor, and the illumination system should include subsystems for controlling the intensity and polarization of the beam, as described herein. TDI sensing is described in detail in U.S. Pat. No. 4,877,326 to Chadwick et al., entitled "Method and Apparatus for Optical Inspection of Substrates", issued Oct. 31, 1989, the entirety of which is incorporated herein by reference. The pixel size changer 703 may include a set of paired Barlow lenses on a slide having a plurality of preset positions.

Beginning with the laser source and following one of the beam paths, FIG. 8 presents a functional depiction of the components used in darkfield imaging. Laser module 801 consists of a 100 mW laser source 801*a* and a beam expander 801*b* for controlling the overall size of the beam. The preferred beam expander is 6×, but other magnification beam expanders could be used to control the beam. Analog light level control mechanism 802 consists of a manually adjusted polarizing beamsplitter 802*a* and a motorized half wave plate 802*b* used in concert as a pair of crossed polarizers. Adjustable turning mirror 803 is used for alignment. Switchable beam de-expander 804 is inserted to adjust the illumination for review purposes, making the beam wider in X and narrower in Y. Adjustable turning mirror 803 and beam translation plate 805 are used for alignment, while polarizing beam splitter 806 splits the beam into two paths. Switchable quarter-wave plate 807 is used for circular polarization, while rotatable half-wave plate 808 is used for S or P polarization control. Cylindrical lens 809 maintains twist and focus control, while beam transition plate 810 is used for alignment. Lens arrangement 811, preferably a set of two Barlow lenses, permit adjustment of the beam to the selected darkfield pixel size. The lens arrangement 811 is preferably on a two position slide for selecting from the two available pixel sizes, but could be on an N position slide. Pixel size may be continuously varied as opposed to discretely available.

Grazing angle mirror arrangement 812 preferably comprises three grazing angle mirrors to direct the beam onto the wafer in the TDI field of view. The grazing angle mirror arrangement 812 provides individual mirror adjustability for height, elevation angle, and azimuth angle. The mirrors are each on a three position translation mechanism for selecting each of the three available angles.

Figure 9:
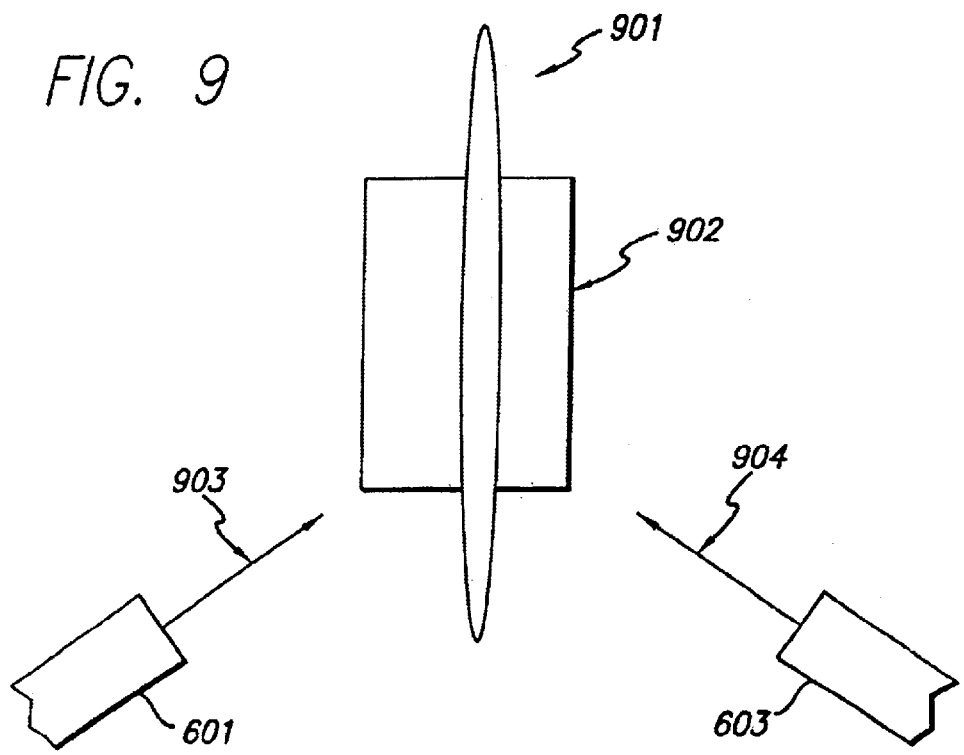
FIG. 9 is a typical arrangement of the dual laser illumination system.

Beam shaping controls control the use of laser power in the field of view. A typical arrangement of the dual laser illumination system is shown in FIG. 9. First laser 601 and second laser 603 provide laser illumination field 901 within the TDI field of view 902 using laser beams 903 and 904. Unlike brightfield illumination where the entire field of view in is flooded with light, the laser illumination in darkfield illumination is confined to a narrow strip, thereby ensuring that as much light as possible is impinging on the TDI field of view 902. The beams are kept narrow in the X direction to maintain the entire beam in X is within the field of view 902. The beam is kept long in the Y direction to provide uniform intensity across the Y dimension of the sensor. Laser power outside the sensor in the Y direction is superfluous, but the arrangement provides uniform illumination with a well controlled wavefront in the field of view 902. The two beams emanating from first laser 601 and second laser 603 are shown overlaid in FIG. 9. While the two beams may not overlay precisely, the two beams may be seen within the field of view 902. The tight beam dimensioning in the X direction allows the two beams to wander while still enabling all laser power in the X direction to be collected by the TDI. Again, darkfield illumination permits collection only if scattering sources exist in the field of view 902.

The beam in FIG. 9 is sized for the field of view 802. Two sets of Barlow lenses, or telescope tubes, exist in the Barlow lens arrangement 911 which change the beam size by a factor of two to enable two darkfield pixel sizes.

The angular orientation and focus or width of the beam in FIG. 9 is a function of the elevation angle. As elevation angle varies, the beam rotates within the field of view 902 of the TDI. Cylindrical lens 909 is used to correct the angular rotation of the beam, and a focus adjustment on cylindrical lens 909 provides control for the width of the beam. Path length from the cylindrical lens 909 to the wafer changes with elevation angle. Twist and focus settings are controlled for each elevation angle so that the beams are maintained in a vertical orientation independent of the elevation angle selected, and beam position and alignment is maintained within the TDI field of view 902.

Review camera 520 performs all beam alignment, and the review camera is prealigned to the TDI in a separate alignment operation. The alignment process aligns the beams in the darkfield module such that they pass through the center of rotation of the cylindrical lenses and reach the lower mirror plugs at an angle normal to the wafer. Lower mirror plugs are thereafter aligned to bring laser beams 601 and 603 to the center of the TDI field of view at an accurate elevation angle. Azimuth angle is then adjusted for one of the beams 601 or 603 to match the azimuth angle of the other laser beam such that the fourier patterns align and the fourier filter 516 can be utilized by both beams.

Darkfield illumination parameters visible to the user/ operator include angle of incidence, polarization, and light level. Angle is a selection of the position of the six mirror rack arrangement, described below, or the lower turning mirrors, which turn the beam from the vertical direction to the grazing incidence on the wafer, as well as adjustment of the cylindrical lens twist and focus to maintain beam orientation and width within the TDI field of view 902.

Polarization includes selection of the position of the switchable quarter-wave plate 807 in or out of the beam path and the position of the rotatable half-wave plate 808. Switchable quarter-wave plate 807 transforms linear to circular polarization, while rotatable half-wave plate 808 rotates incoming polarization, and has rotary positions for S, P, and C polarizations. The C position is halfway between the S and P positions, and the C position must match C polarizations between machines.

The effect of polarization is most pronounced as the illumination angle becomes more grazing. S polarization is most commonly used, particularly at low grazing on rough, opaque wafers, where noise reduction is desired. On wafers having transparent surface films, the scattering behavior of surface defects tends to be influenced by the local thickness of the film. The C, or circular, setting permits a combination of the S and P polarizations to illuminate the wafer and for the two polarizations to average, with less resultant influence from the film thickness. The P polarization produces an anti-node at the wafer surface rather than the node produced with the S polarization.

The system also provides variable illumination adjustability, including adjustability into saturation. The system can specify illumination rather than TDI gray levels, which is useful when local processes cause the light level algorithms to produce increased sensitivity variation over the simple light fixed level. The system further sets sight levels causing saturation in the TDI image. Some features will not subtract well whether or not they saturate, so the illumination strategy is to use as much light as possible and not critically evaluate corners but instead examine the specimen for defects in the open areas. This requires the sensor 304 to be allowed to go deep into saturation without blooming.

Light level adjustment is performed in two stages, fine setting and coarse setting. Fine setting, or analog light level, uses a set of adjustable cross polarizers, while coarse setting, or digital light level, switches in different ND filters. Manually adjusted polarizing beamsplitter 802a of analog light level control mechanism 802 is positioned on a manually rotatable mount set at alignment time to apportion laser power between the two beam paths. Laser light passing into the analog light level control assembly is linearly polarized, and the polarization is rotated by the motorized half wave plate 802b. The resultant linear polarization can range continuously from parallel with the output from the polarizing beamsplitter 802a to orthogonal to it.

The laser light emitted from the beamsplitter 802a has fixed polarization as the output polarizer does not move, and laser power varies sinusoidally from maximum to minimum as the half wave plate rotates. An extinction ratio, representing the ratio from maximum to minimum of approximately 300 to 1 is typically achieved by the analog light level mechanism 802. The output polarization is at approximately 45 degrees to the plane of the darkfield optics module such that downstream polarizing beamsplitters at 90 degrees to the plane of the module can receive half the laser power for each beam path.

The digital light level mechanism consists of a set of three ND filters, preferably two filters plus a clear aperture, providing additional attenuation of zero, 10×, or 100×. This additional attenuation is required to assure that the full dynamic range and resolution of light setting is achievable, preferably a light level range of 1000 to 1 and a resolution of one per cent at any light level setting.

A laser power sensor is positioned downstream from the last polarizing beamsplitter in the optics train. The laser power sensor measures a fixed proportion of the light allowed into the two beam paths, and is therefore a measure of the light level setting from the two light level mechanisms. The laser power sensor is also used to perform a calibration operation on the light level mechanisms.

Calibration of the darkfield illumination system utilizes the laser power sensor, which provides a reading proportional to the illumination in the two beam paths. The calibration consists of rotating the analog light level mechanism 802 to determine light level as a function of angle, then switching the ND filters to find the exact attenuation as a function of each filter. The resultant data is used to create a mapping of percent light level to positions of the analog and digital NDs without gaps or discontinuities.

The system further includes 2 segment Segment Automated Thresholding™, or SAT™. SAT™ automatically separates the digitized wafer image into different regions called "segments" based on process noise and brightness. Peak sensitivity is achieved by assigning separate thresholds to each segment of the image rather than a single threshold for the entire image. Optimal thresholds are automatically determined for each segment based upon the process variability which exists on the inspected wafer. The ability of SAT™ to adapt to changing process conditions provides greater sensitivity to be achieved and maintained wafer-to-wafer and lot-to-lot without nuisance defects.

2 segment SAT™ uses high sensitivity in the extreme upper left corner of the mean/range histogram where the mean and range are low. This area is associated with small defects on a background, where the goal is to optimize the sensitivity in the clear areas and evaluate any information available in the rest of the image.

The brightfield radiation employed in the system of FIG. 5 is broadband flood illumination. The broadband radiation optically averages intensity variations, including interference effects caused by thickness variations in transparent films. Averaging interference effects increases signal-to-noise ratios for higher sensitivity to almost all defect types, including CMP related defects. The result is an improvement in defect detection sensitivity, particularly on wafers having extreme color variations. Broadband flood illumination also provides faster setup times and improved throughput in many applications.

The system may include an anti-vignetting aperture to improve the collection uniformity of the imaging system, thereby reducing the need to correct the image electronically.

Figure 10:
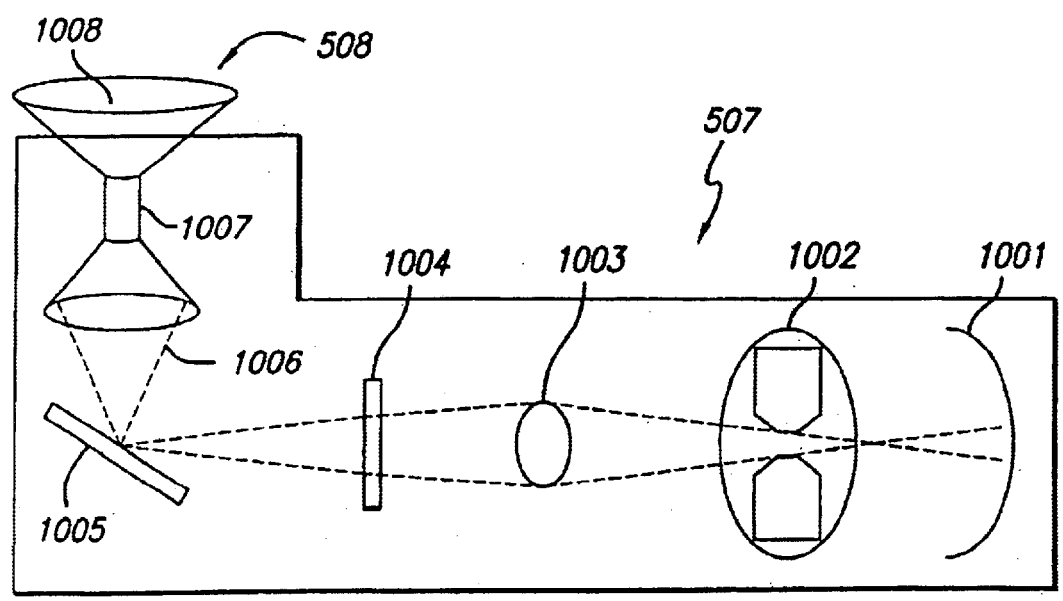
FIG. 10 illustrates an expanded view of the brightfield illuminator.

FIG. 10 is an expanded view of brightfield illuminator 507. Backing mirror 1001 reflects light from arc lamp 1002 through condenser 1003. Upper turning mirror 1004 then passes the light to lower turning mirror 1005, which reflects the light to illuminator lens arrangement 508, which includes 70 mm lens 1006, condenser 1007, and 21 mm lens 1008.

Figure 11:
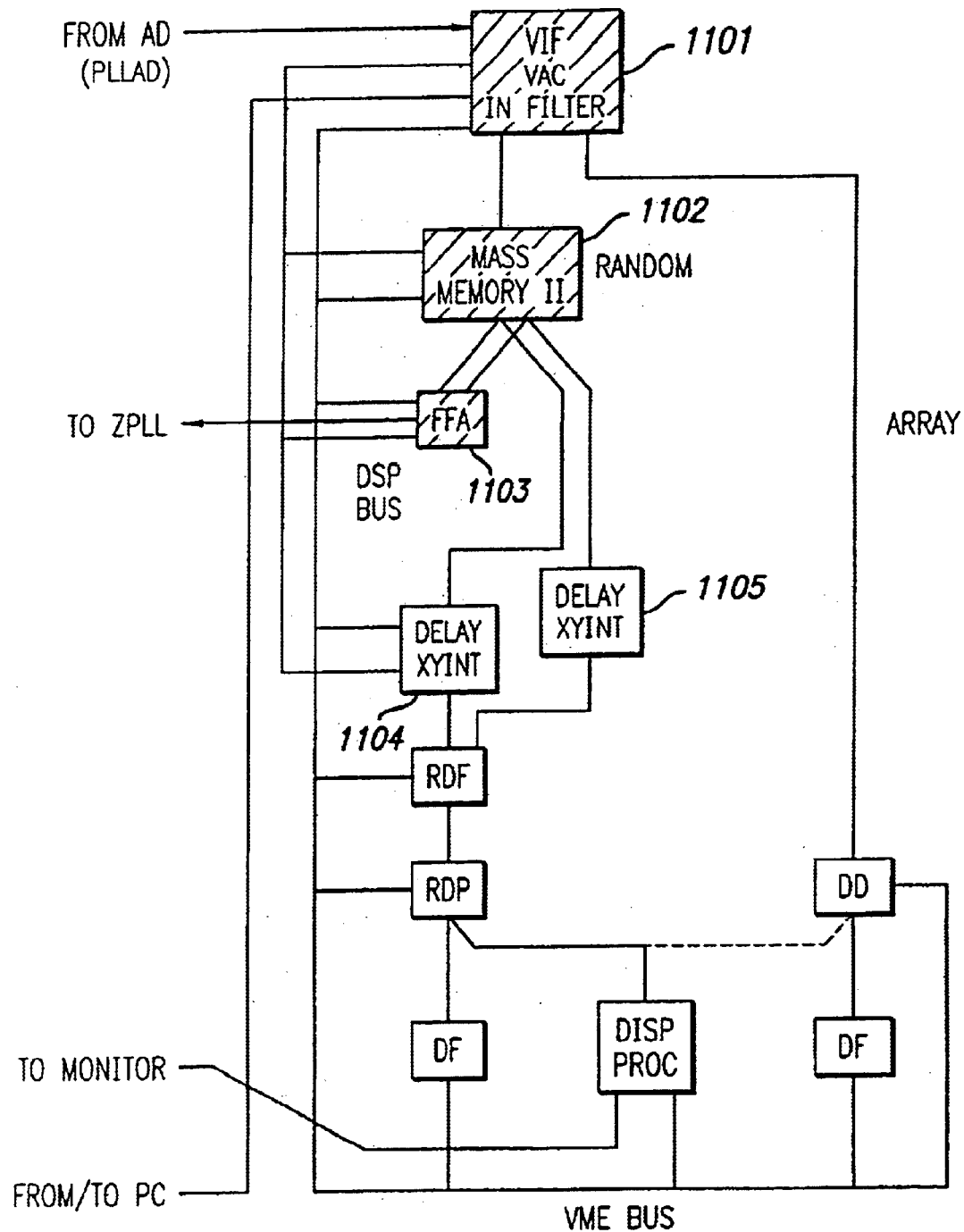
FIG. 11 shows the image computer subsystem architecture.

The image computer subsystem architecture 1100 is presented in FIG. 11. Similar components are available in the KLA-Tencor Corporation Model 2135 unit, with the exception being those components having particular shading. Diagonal shading indicates those components having hardware changes from the 2135, and vertical shading represents a component having embedded code changes. VIF 1101 includes changes in demultiplexing circuitry on the sensor motherboard at the front end of the image computer. The mass memory board 1102, or MM2, is modified to add memory and allow reprocessing of edge die for large pixel darkfield inspections. The mass memory board 1102 memory is organized as odd and even data banks, making it impossible to issue data for two odd or two even dice simultaneously for edge die evaluation. The system modifications add shadow banks of reversed odd and even order, so even die go into the even bank and also to a shadow odd bank that can be used during edge die reprocessing. The amount of mass memory is therefore doubled for the current system over the 2135. The 2135 uses four image computers each having 64 MB of mass memory on each MM2 board, for a total of 256 MB of mass memory. The current system uses a single image computer with a total of 512 MB of mass memory on its only MM2 board. Programmable logic changes accommodate the additional memory banks and allow edge reprocessing.

The FFA 1103, or full field alignment system, firmware accommodates an alignment kernal change from 32×512 pixels to 32×2048 pixels. The XY interpolator (XYI) boards 1104 and 1105 require additional memory as they include a pipeline delay to allow the FFA to calculate alignment errors before the data is corrected by the interpolators. A single pair of XYI boards 1104 and 1105 is utilized in the system to delay and interpolate a swath of data. The 2135 uses four pairs of boards to accomplish this task. The delay capacity on the new boards 1104 and 1105 are therefore increased.

TDI sensing provides a wider range of data collection over previous systems, which could typically collect only a single narrow band of data at one time. TDI provides a wider overall collection area. Pixel size for the TDI sensor 304 of the present system is preferably a 16 micrometer square, but other dimensions may be employed. The smaller pixel reduces the sensor's contribution to the noise budget of the system. The TDI sensor also provides anti blooming capability to permit use of saturating light levels for darkfield inspections. The TDI sensor also provides a current output to accommodate designing for high bandwidth outputs. The system preferably runs at 200 Mpx, but can accommodate at least up to approximately 800 Mpx. The TDI sensor 304 provides more pixels in the shift direction, or X direction, to enable longer integration and a wider illumination field for brightfield at approximately 800 Mpx. The feature is not used in brightfield illumination in the present system, but the additional pixels are used in darkfield illumination to accommodate beam wander without losing illumination efficiency. The additional pixels cannot be used in brightfield since the amount of distortion is proportional to field size, and an increase in the illumination field results in a blurrier TDI image. Brightfield illumination is limited within the system using a field stop in the illumination train to limit the illumination to preferably 256 TDI pixels in the X direction. The number of TDI pixels may vary to a greater or lesser than 16 by 16 range.

Fourier filtering comprises an adjustable array of wire blockages which filters repetitive features in the Y-direction of the TDI image. The fourier filter has adjustable pitch for spacing variance and adjustable offset for position variance to accommodate various fourier patterns or semiconductor arrangements. The formula for the pitch of the diffraction spots in the fourier plane is:

$$F_i = (\lambda * L_f)/(M_{obj} * M_{pc} * A_i)$$

where $F_i$ is the pitch of the spots at the fourier plane in mm, $\lambda$ is the wavelength of the laser in micrometers, $L_f$ is the reference focal length of the objective lenses in mm, which is preferably 200 mm, $M_{obj}$ is the objective lens magnification, which is preferably 10 to 20 for the darkfield pixels, $M_{pc}$ is the power changer magnification (preferably 0.5 or 1), and $A_i$ is the cell size of the array in the Y direction. Again, these dimensions may vary while maintaining adequate performance and still be within the scope of the invention.

Figure 12:
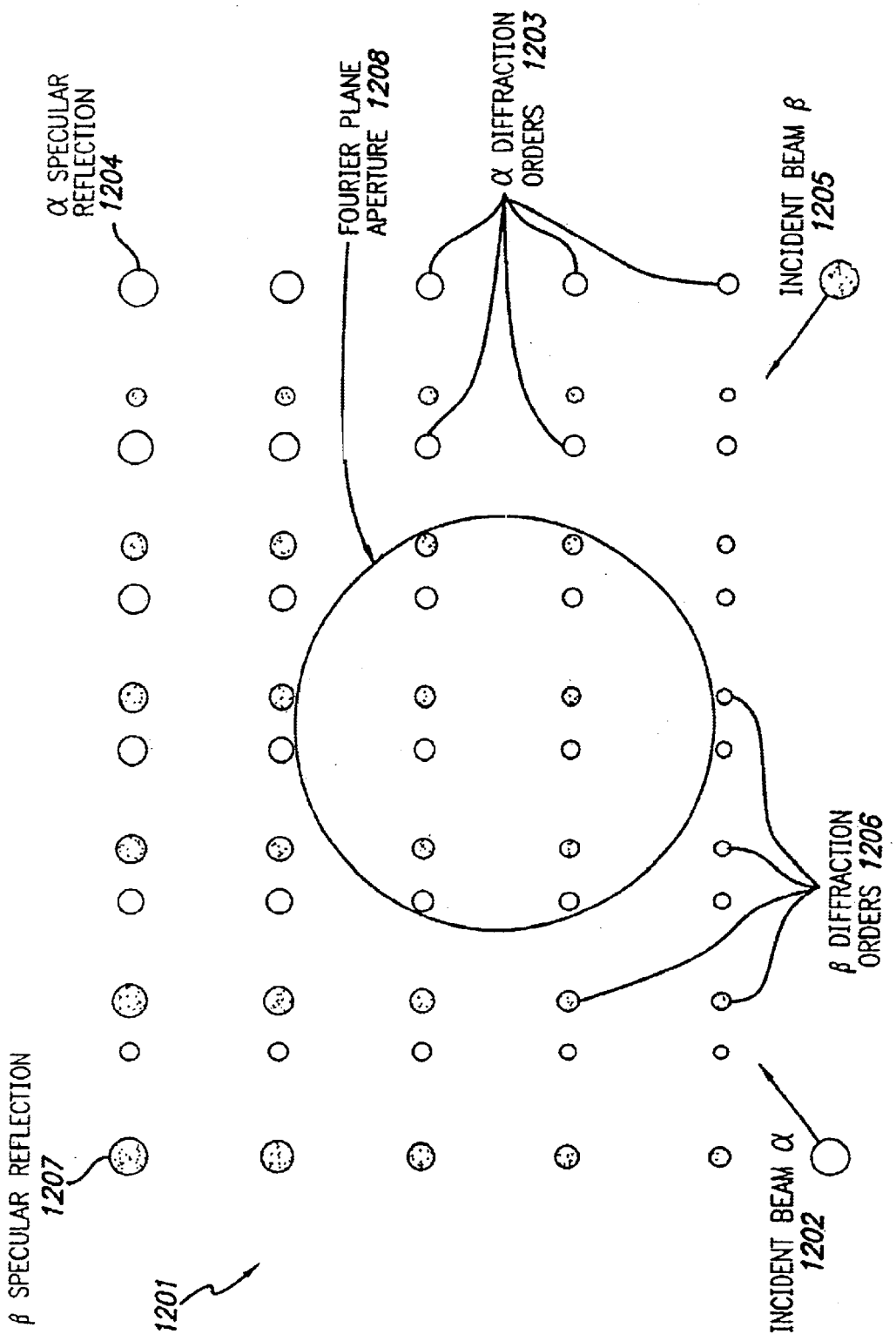
FIG. 12 presents a diagram of the fourier spot patterns created from a typical array as produced by illumination from two laser beams.
Figure 13:
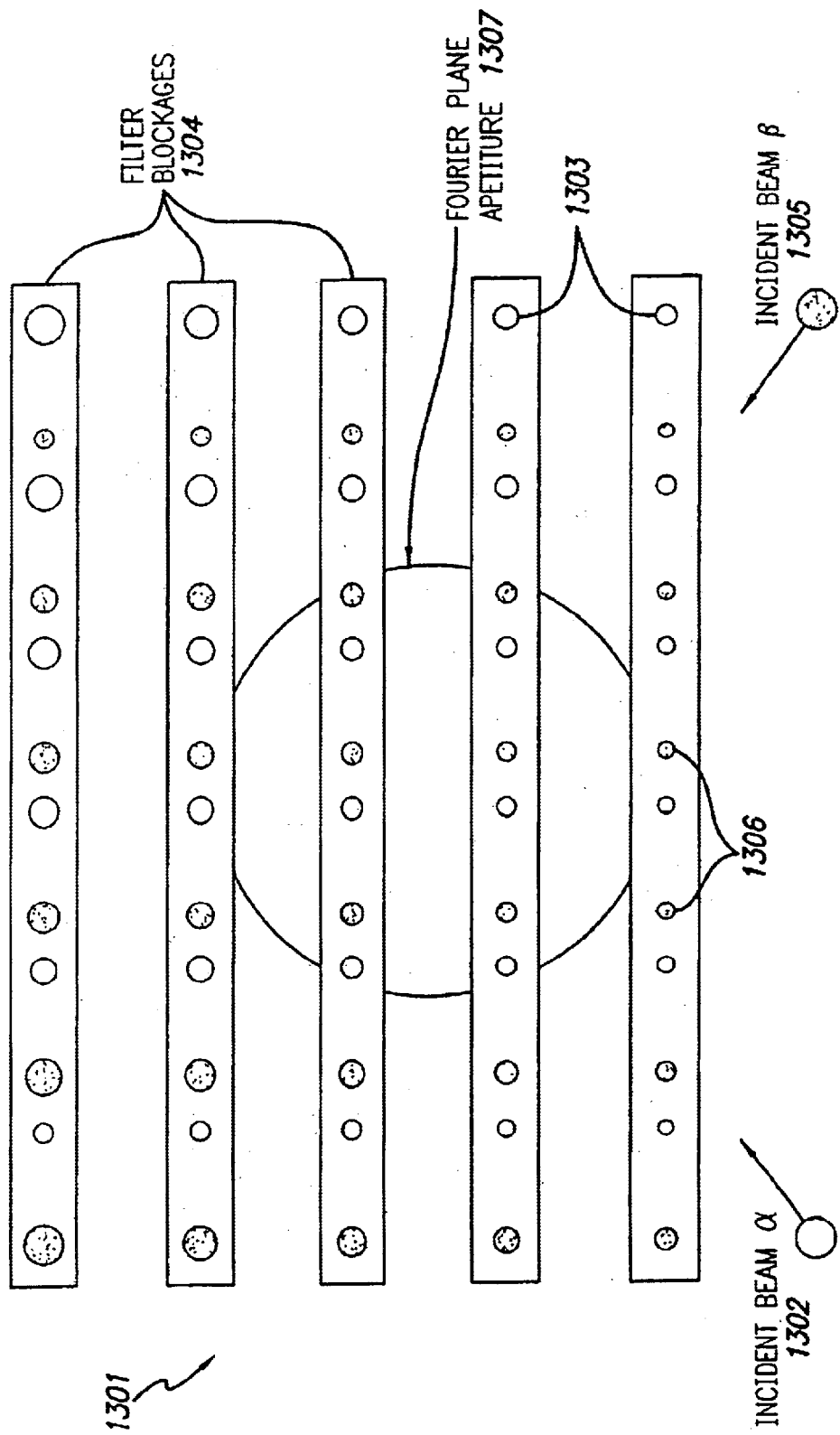
FIG. 13 is another diagram of the fourier spot patterns.

The fourier filter removes the repeating content of an array area but leaves non-repetitive features. This permits clear transmission of defects without the clutter associated with repeating patterns, as a point source defect is spread throughout the fourier plane, so most of the energy passes through the mechanical blockages. A typical fourier filter reading is shown in FIGS. 12 and 13. In FIG. 12, a diagram of the fourier spot patterns 1201 created from a typical array is shown as produced by the illumination of two laser beams, each providing a coherent, collimated beam of light. A beam 1202 of incident laser light α hits the wafer producing the α diffraction orders 1203 and α specular reflection 1204. A beam 1205 of incident laser light β strikes the wafer producing the B diffraction orders 1206 and β specular reflection 1207. A fourier plane aperture 1208 samples the diffraction patterns for α and β.

Size as shown in FIGS. 12 and 13 represent intensity of the diffraction spots. The spots do not actually vary in size as shown, but do vary in intensity. The two shadings distinguish between diffraction spots from the two incident beams.

FIG. 13 illustrates a diagram of the fourier spot patterns 1301 created from the array is shown produced by the illumination of two laser beams. FIG. 13 is a diagram of the diffraction spots and filter blockages at illumination elevation angle theta. A beam 1302 of incident laser light α strikes the wafer producing the α diffraction orders 1303, which are blocked by wires or springs acting as filter blockages 1304. A beam 1305 of incident laser light B strikes the wafer producing the β diffraction orders 1306 also blocked by filter blockages 1304. A fourier plane aperture 1307 samples the diffraction pattern for α and β.

Using fourier filtering, the scatter from surface roughness causes no effect, so if an array of rough metal or rough polysilicon is fourier filtered, the resultant image is of unpatterned rough metal or unpatterned rough polysilicon. An array of noisy material produces a noisy image, so fourier filtering becomes less effective as the array becomes less regular or more rough. The fourier filtering removes spatial frequencies from the image content, affecting the non-repetitive features passing through the filter. To create an image of a point-source defect, all spatial frequencies are required. With certain frequencies removed, the point defect becomes a repeating pattern in the image.

Sidelobes caused by a defect in an array caused by the fourier filter are visible in the darkfield image. The effect of these sidelobes is accounted for and corrected by the system.

The fourier filter 516 operates only in the Y direction and has limited range. The two illumination beams of the system each create a fourier pattern. The spacing of the fourier spots changes inversely with cell size on the wafer and illumination wavelength. Spacing does not change with grazing angle, but the pattern does move or translate as a whole with variations in grazing angle. The fourier pattern for the two illumination beams moves in tandem (in the same direction in Y) when the grazing angle is changed, so a single set of blockages is used for both beams. The fourier patterns also move in the X direction, specifically in opposite directions, with changes in grazing angle. Straight-line blockages in the X direction allow any amount of X direction movement of the spots without impairing filtering ability. The apparent spacing of the blockages is also influenced by optics magnification, with spacing decreasing as magnification increases. Since filter spacing has a limited range, some cell sizes may be filtered at one magnification but not another. Since fourier filter spacing can be made only so small, a maximum array size exists that can be filtered. The maximum cell size is preferably 20 micrometers for the 10×1 optics configuration, 10 micrometers for the 20×1 configuration, and 5 micrometers for the 20×2 configuration, but these values may be altered to maintain adequate overall performance. The fourier filter is set such that settings translate from one machine to another, and where feasible from one optical configuration to another.

The fourier image is developed at the pupil plane behind the power chargers in the imaging path. Using the review camera 520, the fourier plane can be imaged by inserting the Bertrand lens into the review path. The Bertrand lens can be accessed from the review user interface or from superdiags. The diffraction spots and the position of the fourier filter blockages may be monitored by imaging the fourier plane, and this technique can be used to manually adjust the filter to block a particular wafer pattern.

As the system of FIG. 5 utilizes several redundant components in performing both brightfield and darkfield imaging, some components may exist which are beneficial to one form of illumination and not the other. The brightfield beamsplitter 513 provides a benefit to the broadband brightfield imaging described herein, but degrades performance of darkfield imaging. Thus the brightfield beamsplitter is removable, and preferably replaced with a blank, or glass, when performing darkfield illumination. This allows more light to pass to sensor 304 and permits greater levels of detection in darkfield imaging. An alternative method for producing the same result is to perform brightfield imaging in a selected color spectrum and performing darkfield in a different frequency color spectrum. For example, if brightfield illuminator 507 or any component along the path prior to the beamsplitter used red light, the darkfield imaging components, such as the lasers 601 and 603 would use green light, where red light and green light have different frequencies. Such an implementation removes the negative effects associated with the brightfield beamsplitter 513 when used for darkfield imaging.

The brightfield optics are thus similar to those used in the KLA-Tencor Corporation Model 2135. The autofocus system is identical in the present system. The brightfield illumination system has an additional shutter and field stop. The imaging path preferably includes a new 20× objective 515, and the objective 515 allows high angle laser incidence. A higher or lower magnification objective may be used while still within the scope of the invention. The brightfield beamsplitter 513, as discussed herein, is removable to improve darkfield collection efficiency.

Power changers which provide for a larger fourier plane are used in the present system. The increased power changers yield the magnification of the tubes scaling back by a factor of two so that the size of the fourier plane scales upward by a factor of two. The power changers in the present system thus preferably have magnifications of approximately 0.5× and 1×, but other values are available, such as between the ranges of 0.25× and 1×. The magnifications are compensated for in the zoom mag and TDI pixel size. The tube improvements include optimizing the quality of the fourier image to minimize distortions so that the fourier blockages are as small as possible. The system further has the ability to match the fourier plane focus between the approximately 0.5× and 1× tubes, so that the same fourier position is used for both tubes. The 0.5× power changer is used for darkfield inspections, but the 1× tube is also used for darkfield rearview, so the fourier filter may be used with both power changers. Fourier focus matching requires an axial focus adjustment for the 0.5× power changer. Again, other magnitude components may be used while maintaining performance and still be within the scope of the invention.

The system further includes a Y mirror having a slightly larger mirror aperture and a small displacement of the mirror assembly to provide room for the fourier filter. The zoom assembly corrects magnification differences between the present system and other system imaging optics. Again, the TDI sensor produces lower noise and anti-blooming capability, and the review optics of the new system match the present system magnifications to other systems.

Figure 14:
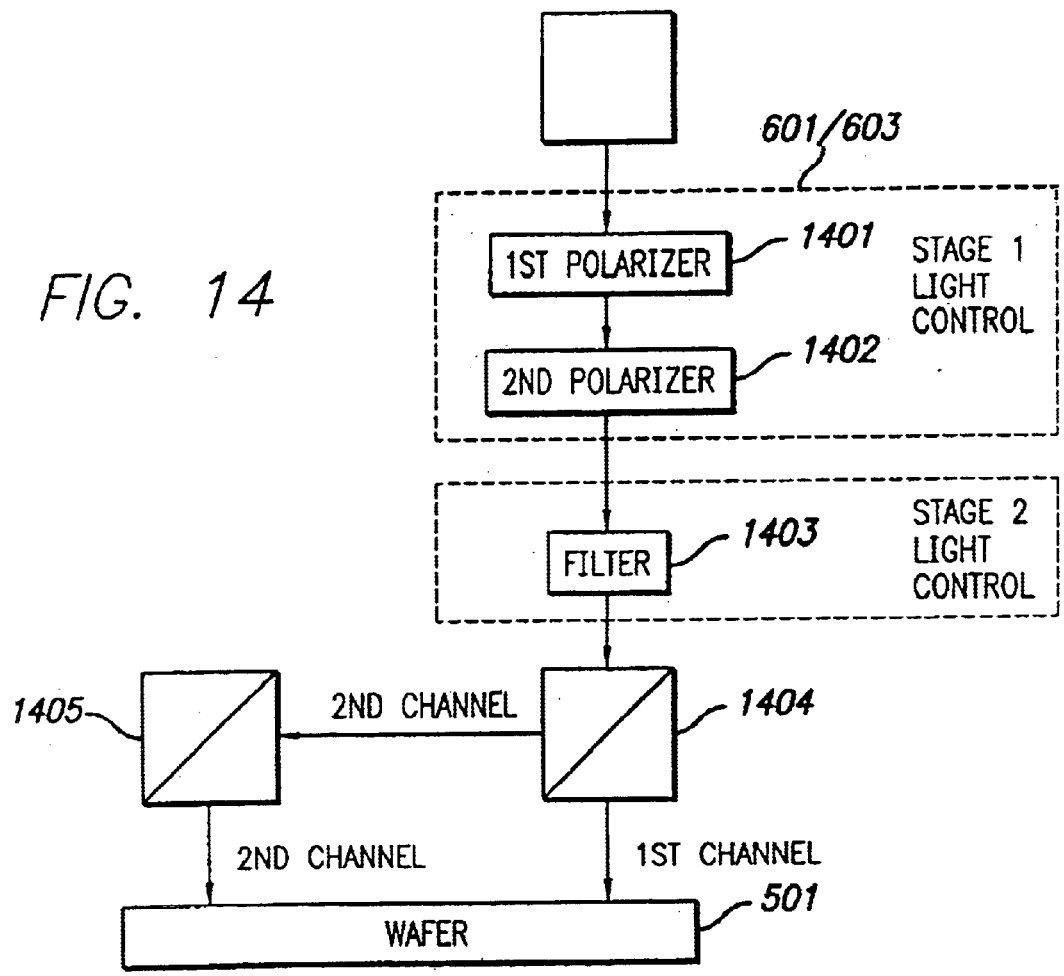
FIG. 14 illustrates light level control for the system.

The light level control for the system is illustrated in FIG. 14. Laser 601 or 603 generates a laser beam, which passes through a first polarizer 1401 and a second polarizer 11402. The polarizers are rotated relative to one another to control the intensity of the beam passing through them. The combination of polarizers 1401 and 1402 comprises the first stage of light level control. The relative rotation of the polarizers 1401 and 1402 provides variation of the beam intensity in a continuous manner, preferably without varying the polarization of the beam.

Rotation of polarizer 1402 controls the balance between the two output channels. The channels are preferably balanced to provide two laser lines of similar intensity on the surface of the substrate. The lines may be oriented at an angle relative to one another such that they will provide adequate illumination for various substrate topographies.

Light exiting from polarizer 1402 passes through filter 1403, which is preferably a discrete glass filter. Filter 1403 absorbs a portion of the light. The filter may be selected from a set of filters included within the system, and may filter the light intensity by 100 to 1, 10 to 1, 1 to 1, or some other quantity. The filter 1403 comprises the second stage of light control.

The beam then passes through a polarizing beamsplitter 1404, which divides the light into first and second channels. The second channel is further reflected and polarized, as needed, as represented in FIG. 14 as element 1405, and both beams thereafter illuminate the substrate. Both beams preferably have equal intensity as they impinge on the substrate surface.

A laser power sensor may be used to monitor laser power delivered to the wafer 501. This laser power sensor may be used in a feedback loop to control the system light level. As noted above, the laser power sensor is positioned downstream from the polarizing beamsplitter, and the laser power sensor measures leakage from the beamsplitter. Leakage measurement thereby measures a fixed portion of the light allowed into the two channels. Signals from the laser power sensor can be used to control both stages of the light level control. The system is initially calibrated to verify the functionality of the feedback loop and make appropriate adjustments.

While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

We claim:

1. An apparatus for inspecting a specimen, said apparatus comprising:
   a broadband brightfield illuminator for providing brightfield illumination of said specimen;
   at least one light emitting device for providing darkfield illumination of said specimen;
   a pattern remover having the ability to remove predetermined patterns from data received from said broadband brightfield illuminator and said at least one light emitting device; and
   an anti-blooming sensor for sensing data received from said specimen.

2. The apparatus of claim 1, wherein the anti-blooming sensor comprises a time delay integration sensor with anti-blooming capability.

3. The apparatus of claim 1, wherein said at least one light emitting device each have a predetermined azimuth offset from one another and energy emitted from said at least one light emitting device is angularly adjustable.

4. The apparatus of claim 1, wherein said at least one light emitting device illuminates a predetermined region on the specimen.

5. The apparatus of claim 4, wherein the apparatus forms an angular image of the illuminated region and transmits light representative of the image towards the sensor.

6. The apparatus of claim 1, wherein said anti-blooming sensor comprises a detector having a sensing surface for receiving collected light and generating data representative thereof.

7. The apparatus of claim 1, wherein the anti-blooming sensor collects light scattered from an illumination region on said specimen with a predetermined collection angle.

8. The apparatus of claim 7, wherein the pattern remover comprises a filter operable to selectively separate at least one light component.

9. The apparatus of claim 1, wherein said anti-blooming sensor permits use of saturating light levels for darkfield inspections.

10. The apparatus of claim 1, wherein the anti-blooming sensor provides a current output to accommodate high bandwidth outputs.

11. The apparatus of claim 1, wherein the anti-blooming sensor runs at least up to approximately 800 Mpx.

12. The apparatus of claim 1, wherein the anti-blooming sensor provides more pixels in the shift direction to enable longer integration and a wider illumination field for brightfield.

13. The apparatus of claim 1, wherein the anti-blooming sensor accommodates beam wander without losing significant illumination efficiency.

14. An apparatus for inspecting a semiconductor wafer specimen, comprising:
   a brightfield illumination arrangement employed during a first inspection of the semiconductor wafer specimen;
   a darkfield illumination arrangement employing a laser and performing a second inspection of the semiconductor wafer specimen, said second inspection separated in time from said first inspection; and
   an anti-blooming TDI sensor for receiving selected darkfield illumination transmitted from said brightfield illumination arrangement during said second inspection and brightfield illumination transmitted from said brightfield illumination arrangement during said first inspection and reflected from said semiconductor wafer specimen.

15. The apparatus of claim 14, wherein energy emitted from said darkfield illumination arrangement is angularly adjustable.

16. The apparatus of claim 14, wherein said darkfield illumination arrangement has the ability to illuminate a first predetermined region on the specimen.

17. The apparatus of claim 14, wherein said darkfield illumination arrangement has the ability to illuminate a second predetermined region on the specimen.

18. The apparatus of claim 14, wherein said anti-blooming TDI sensor comprises a detector having a sensing surface for receiving collected light and generating data representative thereof.

19. The apparatus of claim 14, wherein the anti-blooming TDI sensor collects light scattered from an illumination region on said semiconductor wafer specimen with a predetermined collection angle.

20. The apparatus of claim 14, said apparatus comprising an optical path over which reflected light from said semiconductor wafer specimen travels, said apparatus further comprising a filter operable in the to selectively separate at least one light component from light energy reflected from the semiconductor wafer specimen.

21. The apparatus of claim 20, wherein the apparatus forms an angular image of the illuminated region and transmits light representative of the image towards the anti-blooming TDI sensor.

22. The apparatus of claim 14, wherein said anti-blooming TDI sensor permits use of saturating light levels for darkfield inspections.

23. The apparatus of claim 14, wherein the anti-blooming TDI sensor provides a current output to accommodate high bandwidth outputs.

24. The apparatus of 14, wherein the anti-blooming TDI sensor runs at least up to approximately 800 MPX.

25. The apparatus of claim 14, wherein the anti-blooming TDI sensor provides more pixels in the shift direction to enable longer integration and a wider illumination field for brightfield.

26. The apparatus of claim 14, wherein the anti-blooming TDI sensor accommodates beam wander without losing illumination efficiency.

27. A method for inspecting a specimen, comprising:
    commencing at least one mode of illumination of said specimen, 1, wherein said mode of illumination comprises transmitting light energy toward said specimen and reflecting light energy from said specimen as specimen reflected energy;
    providing an indication when one illumination mode is complete; and
    sensing said specimen reflected energy using an anti-blooming TDI sensor.

28. The method of claim 27, wherein one available mode of illumination comprises broadband brightfield illumination.

29. The method of claim 27, wherein one available mode of illumination comprises darkfield illumination.

30. The method of claim 27, further comprising:
    creating a combined scan representation of said specimen using data from all illumination modes employed;
    wherein said creating occurs subsequent to said sensing.

31. The method of claim 30, wherein two modes of illumination are employed, and wherein said combined scan representation comprises a two dimensional histogram having results from a first predetermined mode of illumination along one axis and results from a subsequent predetermined mode of illumination along a second axis.

32. The method of claim 27, wherein said creating further comprises:
    comparing ideal images with received images;
    preparing a two dimensional histogram of the received images; and
    performing a decision algorithm to determine defects in said specimen.

33. The method of claim 27, wherein said commencing comprises illuminating successive regions of said specimen.

34. The method of claim 27, further comprising collecting light scattered from the illuminated specimen at a predetermined collection angle.

35. The method of claim 27, further comprising selectively separating from light collected by said anti-blooming TDI sensor at least one light component aspect.

* * * * *